United States Patent [19]
Bower

[11] Patent Number: 5,514,576
[45] Date of Patent: May 7, 1996

[54] CLONED PULLULANASE

[75] Inventor: Patricia A. Bower, Milwaukee, Wis.

[73] Assignee: Miller Brewing Company, Milwaukee, Wis.

[21] Appl. No.: 365,189

[22] Filed: Dec. 28, 1994

Related U.S. Application Data

[63] Continuation of Ser. No. 132,648, Oct. 5, 1993, abandoned.

[51] Int. Cl.[6] .......................... C12N 9/44; C12N 15/56; C12N 15/75; C12N 15/81
[52] U.S. Cl. .................. 435/210; 435/69.1; 435/252.3; 435/252.31; 435/252.33; 435/254.21; 435/320.1; 536/23.2
[58] Field of Search ................ 435/210, 252.3, 435/252.33, 254.21, 320.1, 69.1; 536/23.2, 23.6

[56] References Cited

U.S. PATENT DOCUMENTS

| | | | |
|---|---|---|---|
| 4,289,690 | 9/1981 | Pestka et al. | 530/351 |
| 4,355,047 | 10/1982 | Line et al. | 426/13 |
| 4,355,110 | 10/1982 | Line et al. | 435/210 |

FOREIGN PATENT DOCUMENTS

| | | | |
|---|---|---|---|
| 0034470 | 8/1981 | European Pat. Off. | C12N 15/00 |
| 0127291 | 12/1984 | European Pat. Off. | C12P 19/20 |
| 0206783 | 12/1986 | European Pat. Off. | |

OTHER PUBLICATIONS

PCT International Search Report for application No. PCT/US94/11242, 1995, (corresponds to U.S. Ser. No. 08/365,189).

Alberts et al. *Molecular Biology of the Gene*, Garland Publishing, Inc. N.Y., 1983, pp. 185–196.

Yamada, J. 1981, Agric. Biol. Chem. 45 (5):1269–1270.

Emr et al. 1983, Proc. Natl. Acad. Sci. 80:7080–7084.

Janse et al. 1993. Curr. Genet. 24:32–37.

McBride et al. (Dialog File 357 Abstract DBA Accession No.: 89–12852) 1989. Biochem. Soc. Trans. 17(1):229–230.

Wozney, J. M. 1990. Methods in Enzymology 182:738–749.

Kuriki, et al., 170 *J. Bacteriology* 1554 (1988).

Takazawa, et al., 49 *Applied & Environ. Micro.* 294 (1985).

Katsuragi, et al., 169 *J. Bacteriology* 2301 (1987).

Pongr, S. 1987, Methods in Enzymology 154:450–473.

Murray, E. E., et al., 1989, Nucleic Acids Research, 17(2), 477–498. "Codon Usage in Plant Genes".

*Primary Examiner*—Charles L. Patterson, Jr.
*Assistant Examiner*—William W. Moore
*Attorney, Agent, or Firm*—Quarles & Brady

[57] ABSTRACT

A method is disclosed for the expression of an active pullulanase enzyme in a microorganism host. In one aspect, a DNA construct contains a sequence encoding the pullulanase enzyme, except for the nucleotides necessary to encode the first two amino acids in mature pullulanase, and regulating sequences allowing expression of the coding sequence in a microorganism host. An advantageous DNA construct contains regulatory sequences permitting expression of the pullulanase in a yeast cell.

22 Claims, 4 Drawing Sheets

```
pSEY210

MFα1-SUC2                       Pullulanase
   Glu Ala Glu Ala Phe             Gln Gly Phe Val
---GAG GCT GAA GCT TTC----         CAG GGG TTC GTG-----------
           HindIII MFα1 prepro                     Pullulanase
   Glu Ala Glu Ala                         Phe Val
---GAG GCT GA                       AGCT TTC GTG----------
---CTC CGA CTT CGA                       AAG CAC----------

MFα1                  Pullulanase
   Glu Ala Glu Ala Phe Val
---GAG GCT GAA GCT TTC GTG----------
---CTC CGA CTT CGA AAG CAC----------
                  HindIII
```

CLONED PULLULANASE

This application is a continuation of application Ser. No. 08/132,648, filed Oct. 5, 1993, now abandoned.

FIELD OF THE INVENTION

The present invention relates generally to the manipulation of genetic materials and particularly to the manufacture and use of specific DNA sequences useful in recombinant procedures to secure the production of peptides having one or more of the properties of pullulanase enzymes. More particularly, the present invention relates to a method for the expression of pullulanase enzymes in yeast.

BACKGROUND OF THE INVENTION

Pullulanase is a debranching enzyme which can be used in the brewing industry to make low calorie beer and in the beverage industry to make high dextrose syrups. See, for example, U.S. Pat. Nos. 4,355,110 and 4,355,047. These patents, as well as any other patents and/or references hereinafter referred to, are hereby incorporated by reference as if fully set forth herein.

The pullulanase gene has been isolated, sequenced and characterized from bacterial organisms. For example, see, Kuriki, et al., 170 *J. Bacteriology*, 1554 (1988). Rice and other grains have been known to contain pullulanase. For instance, U.S. Pat. No. 4,355,110 discloses the presence of pullulanase in rice.

The pullulanase enzyme can be isolated from rice by the method disclosed in U.S. Pat. No. 4,355,110. One problem with this approach, however, is that a great deal of waste byproduct is generated. One is therefore faced with disposal problems associated with this waste.

Another alternative source of pullulanase is from bacterial cultures. However, the use of bacteria may have certain negative connotations with the public. Also, bacterial pullulanase is generally less active than rice pullulanase.

Accordingly, there is a need for an alternative supply of rice pullulanase enzyme for use in making low calorie beer or high dextrose syrups. The present invention overcomes the aforementioned problems in providing a yeast that is made to express, properly process, and secrete the rice pullulanase enzyme.

Yeast is considered to be a better host organism for the production of food processing ingredients because it is generally regarded as safe and it can be made to express, properly process and secrete certain heterologous proteins. The problem is that some proteins cannot be produced in yeast (for example, some are toxic) and others cannot be properly processed and/or secreted. Each protein must be handled on a case-by-case basis with the probability of success impossible to predict a priori.

The present invention overcomes these problems by providing an expression construct that is capable of directing the expression of a mature pullulanase enzyme in yeast. The invention is more surprising in that the construct expresses an enzyme that does not mimic the natural rice pullulanase amino acid sequence.

The phrase "mature pullulanase" refers to the pullulanase isolated from rice seed. In the mature pullulanase the methionine or a peptide containing the methionine is assumed to have been removed during post translational modification. However, the mRNA sequence must have a methionine residue encoded since it is the translation initiation codon. This is one of the problems that had to be overcome when expressing the pullulanase enzyme in a yeast system as in the present invention.

SUMMARY OF THE INVENTION

One aspect of the invention provides a DNA construct capable of expressing an active pullulanase enzyme which comprises a sequence encoding the pullulanase enzyme, wherein the sequence does not include the nucleotides necessary to encode the first two amino acids in mature pullulanase, and regulatory sequences allowing expression and secretion of the coding sequence in a microorganism host.

A preferred aspect of the invention is the above DNA construct having regulatory sequences which permit expression and secretion in yeast.

Another preferred aspect of the invention is the DNA construct having the coding sequences of SEQ ID NO: 2 and, still more preferred, wherein the regulatory sequences include the promoter and secretion signals from the yeast structural gene, MFα1, which encodes the α-factor mating pheromone.

Another aspect of the invention is a cloned pullulanase enzyme wherein the pullulanase does not contain the first two amino acids of mature pullulanase.

Still another aspect of the invention is a DNA construct comprising a coding sequence homologous to that of SEQ ID NO: 7 wherein the homology is sufficient so that the gene is capable of expressing an active pullulanase enzyme. A preferred coding sequence is one comprising SEQ ID NO: 7.

The invention thus provides a DNA construct capable of expressing and secreting an active pullulanase enzyme and a cloned pullulanase lacking the first two amino acids of mature pullulanase. The active pullulanase of this invention is useful in low calorie beer and high dextrose syrup manufacturing.

One advantage of the present invention is that active pullulanase enzyme may be obtained from non-bacterial hosts and without the waste associated with isolation of the enzyme from rice.

These and still other objects and advantages of the present invention will be apparent from the descriptions below.

DESCRIPTION OF THE INVENTION

A. In General

The present invention is a DNA construct capable of expressing and secreting an active pullulanase enzyme. In one embodiment, this construct contains a pullulanase coding region that is missing the region encoding the first two amino acids of mature pullulanase. The construct also contains regulatory regions suitable to express the cloned pullulanase in microorganisms. Preferably, the microorganism is yeast and the regulatory regions include the MFα1 promoter and secretion leader sequences (which contains the translational initiation codon methionine) and termination and polyadenylation signals.

In brief, the present invention is preferably created by isolating both pullulanase genomic and cDNA clones. However, those skilled in the art of microbiology will envision other possible biochemical methods to derive the genetic construct and amino acid sequence described below such as antibody and homology screening.

The Examples below also disclose a preferable method of creating the fusion between the yeast MFα1 promoter and secretion signal and the pullulanase cDNA to create the two amino acid deletion preferred for the present invention. In this Example, a 5'-region of the genomic clone was amplified using a primer that contained nucleotide sequences necessary to connect the pullulanase sequence at the third amino acid to the MFα1 promoter/signal sequence. However, if other regulatory regions or a different expression system, e.g. ADHI, were required these regions could also be attached to a primer containing nucleotides corresponding to the pullulanase sequence beginning with the third amino acid or any amino acid in the pullulanase sequence including adding additional amino acids to the mature pullulanase. In this manner, one would obtain an expression construct, as in the present invention, which would be the sequence of the pullulanase gene minus the first two amino acids or mature pullulanase with various amino acid additions or deletions to the amino terminal end.

Once the expression construct of the pullulanase enzyme is obtained, it is necessary that this expression construct be placed in a suitable vector containing appropriate sequences required for the propagation of the vector in a yeast host.

B. Creation Of A Pullulanase cDNA Clone

The Examples below disclose the creation of an especially suitable pullulanase coding region. As the Examples disclose, one first isolates a pullulanase gene. Preferably, the isolation is of a rice pullulanase gene.

As in the Examples below, one would first isolate genomic DNA from the pullulanase-containing organism, digest this DNA with restriction endonucleases and insert these DNA fragments into suitable vectors. These genomic clones would be screened with a probe created using the known amino acid or nucleotide sequence of the pullulanase gene or enzyme to determine which clones contained the pullulanase gene. SEQ ID NO: 1 describes the sequence of the mature pullulanase gene. The Examples below disclose a preferred method for screening the genomic clones.

To create a pullulanase cDNA clone, one would most preferably proceed as in the Examples below. cDNA is prepared from rice mRNA by methods known in the art. This cDNA is inserted into suitable vectors and screened for the presence of pullulanase-containing clones. The examples below describe the screening of cDNA library with two genomic DNA fragments.

After cDNA clones have been created that contain both the 5'-end and 3'-end of pullulanase, an expression construct is typically created. By "expression construct" we mean a nucleotide sequence designed to be translated into an active pullulanase gene. For example, the expression construct would not contain introns found in the genomic clone. SEQ ID NO: 2 lacks the first amino acids of the native protein but contains suitable 3' sequences. It is SEQ ID NO: 2 which is the preferred expression construct of the present invention.

Figure 1:
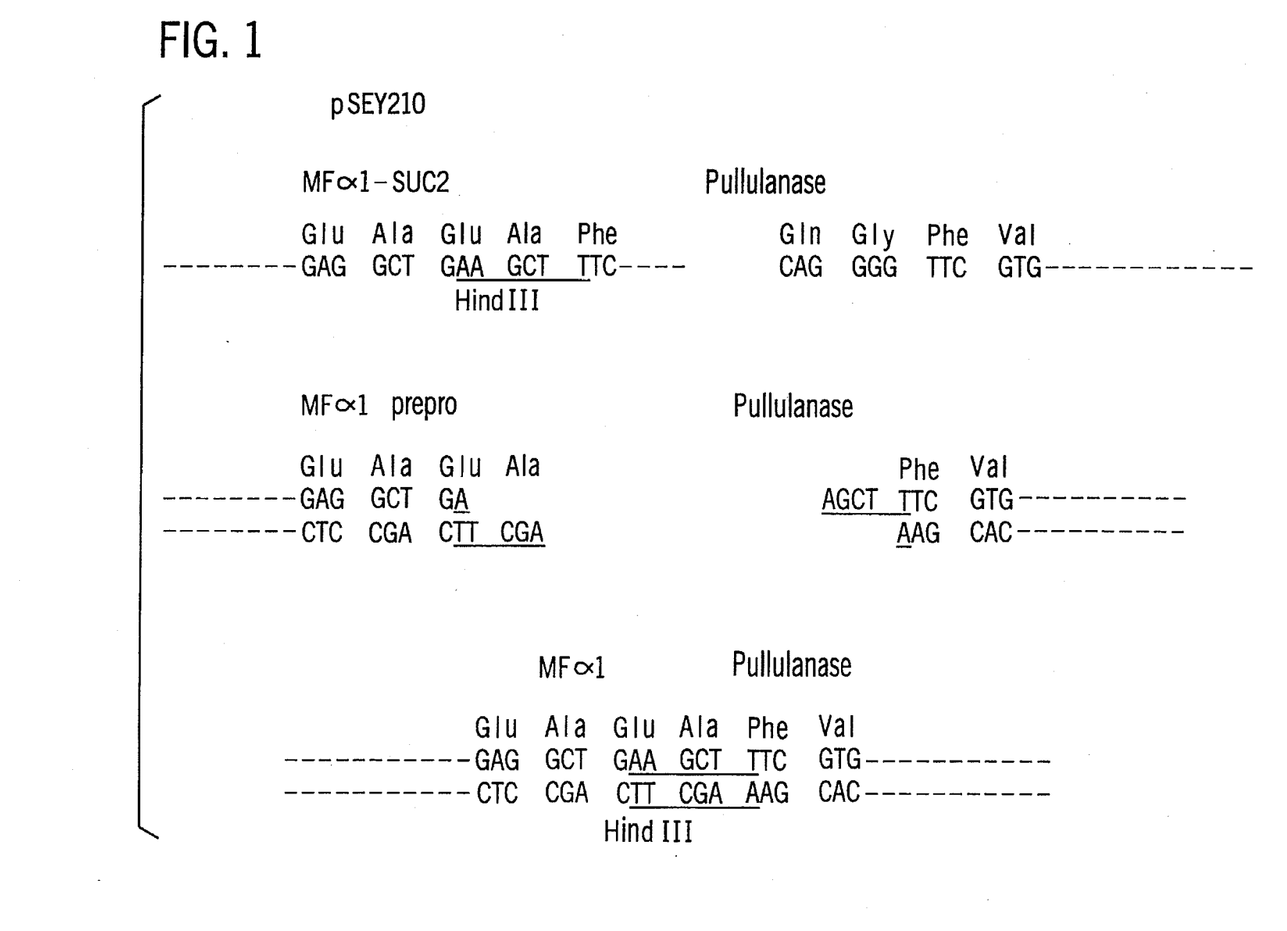
FIG. 1 is a schematic diagram of the amino acid sequence generated when a pullulanase clone is attached to an MFα1 sequence in pSEY210.

The Examples below disclose a preferred method of creating such a construct. In the Examples, the 147 nucleotide 5'-end of the pullulanase gene was amplified via standard PCR methods, using pullulanase genomic clone 9-2 as the target DNA, in such a manner that the first two amino acids were absent after amplification. This was done by use of a PCR primer that contained a HindIII site and a nucleotide sequence beginning with the third amino acid of native pullulanase. FIG. 1 in the examples below and SEQ ID NOs:3 and 4 describe preferable primers.

Next, the 3'-end of the pullulanase gene is amplified using cDNA clone 6-1 as the target DNA. The examples below disclose that a 0.7 kb fragment is created. In this example the fragment also contains part of the 3' untranslated region which contains the rice transcriptional termination and polyadenylation signals. These structures are similar in sequence to the yeast structures and may function in yeast. Both transcriptional termination and polyadenylation signals have been shown to be necessary for proper expression in yeast (Romanos et al. YEAST 8:423 (1992)).

These two fragments are combined by methods known in the art via appropriate restriction sites with a 2.3 kb portion of the pullulanase cDNA clone to create a full-length pullulanase expression construct. The resulting expression construct contains the exact coding sequence for the pullulanase enzyme with the exception of the omission of the first two amino acids.

Preferably, the expression construct is placed in a vector containing suitable sequences for expression in a yeast system (as discussed above) or as an autonomously replicating plasmid or integrated into the host chromosome. An especially preferred vector is pSEY210 which contains MFα1 promoter and secretion leader sequences but no transcriptional termination or polyadenylation signal.

Once the expression construct is created, one will have to express it and test for pullulanase activity. The Examples below disclose appropriate expression strategies. The enzymatic assay is also most preferably done as described below, although other assays designed to evaluate the activity of a pullulanase enzyme would be equally appropriate.

C. Microorganism Hosts

The pullulanase expression construct of the present invention is capable of expression in other suitable microorganism hosts. One would obtain the DNA region containing the pullulanase coding region (the "expression construct") and insert it in a suitable vector containing suitable regulatory signals for other microorganism hosts. Representative examples would include *E. coli, Bacillus, Aspergillus, Pichia,* or *Kluyveromyces.*

EXAMPLES

A. In General

The Examples below disclose the creation, isolation, and characterization of a pullulanase-specific probe; the isolation and characterization of pullulanase genomic and cDNA clones from a rice genomic and cDNA libraries; and the creation of a pullulanase expression construct. The expression construct is obtained by amplification of 3' and 5' segments of the pullulanase cDNA and genomic clones, respectively, and combination of these amplified fragments with a pullulanase cDNA clone. This expression construct does not contain the first two amino acids of mature pullulanase.

This expression construct was placed in a yeast expression vector, pSEY210. From this vector, active pullulanase enzyme was expressed and measured.

B. Creation of Pullulanase Genomic and cDNA Clones

1. Isolation of a Pullulanase Specific Probe

The preferred method relies on amino acid sequence information from the pullulanase protein and peptide fragments generated by cyanogen bromide digestion and PCR technology to isolate a pullulanase specific probe. Using this probe both rice genomic and cDNA libraries can be screened for pullulanase genes. Three CNBr pullulanase peptide fragments were isolated and partial amino acid sequences were determined.

a. Pullulanase Amino Acid And PCR Primer Sequences

Rice genomic DNA was amplified using PCR technology with mixed oligonucleotide primers based on the amino acid sequence information from the pullulanase amino-terminal end and a 41.0 kd pullulanase CNBr peptide. Under these PCR conditions (below), primers 20-5' (SEQ ID NO: 8) and 41-3'b (SEQ ID NO: 9), an approximately 675 bp genomic PCR product was isolated. PCR primers were made for two other CNBr fragments but they produced no PCR products. The 675 bp PCR product was subcloned into an appropriate vector (in this case the SmaI site of bacterial vector pUC18) and DNA sequence analysis confirmed, based on a comparison with the amino-terminal amino acid sequence data of pullulanase, it contained a portion of the amino-terminal end of the pullulanase gene. This probe was designated pul-1.

b. PCR Conditions

PCR amplifications were done using the GeneAmp DNA amplification kit according to the instructions of Perkin-Elmer Cetus and a Perkin-Elmer Cetus DNA Thermal Cycler. The following conditions were used: One microgram of rice genomic DNA (boiled before use to facilitate PCR reaction) and one microgram each of amino-terminal primer SEQ ID NO: 8 and 9 were added to the reaction mix and amplified using the following temperature profile: (one cycle) 95° C. for 2 min.; (30 cycles) 94° C. 1 min., 55° C. 1 min., 72° C. 3 min.; (one cycle) 72° C. 10 min. Due to the complexity of the rice genome, a ten microliter aliquot of the first PCR amplification reaction mixture was taken and amplified a second time using the same PCR conditions and primer concentrations as before.

2. Screening the Rice Genomic and cDNA Libraries

A rice genomic library (*Oryza sativa* L. (indica) var. IR 36), constructed in Lambda phage EMBL-3 SP6/T7, was purchased from Clontech, Palo Alto, Calif. The library was screened as outlined in Maniatis, et al., Molecular Cloning: A Laboratory Manual (1982). The hybridization probe (pul-1) was isolated (GeneClean, Bio 101, LaJolla, Calif.) as a KpnI/BamHI fragment from pUC18 and radioactively labelled using the Dupont/NEN Research Products (MA) [$^{32}$P] dCTP-nick translation system. High titer lysates were prepared from "tentative" pullulanase-positive recombinant phage (Silhavy, et al., *Experiments with Gene Fusions* (1984)) and several clones were chosen for a second screening.

3. Characterization of "Tentative" Rice Pullulanase Genomic Clones a. Method

Four "tentative" pullulanase clones were chosen, based on the strength of the initial hybridization signal, for restriction enzyme mapping. Recombinant phage were isolated, by ultracentrifugation, from 50 milliliter lysates. The phage DNA was extracted from the phage pellet using phenol/chloroform. The pullulanase PCR fragment (pul- 1) was used to determine the restriction map of the clones. Because pul-1 represents the amino-terminal end of the pullulanase, the restriction fragment containing the amino-terminal end of each genomic clone was readily identifiable.

b. Analyses i. Restriction Enzyme Digestion

Because genomic clone 9-2 contained the largest DNA insert, it was chosen for complete restriction enzyme mapping. When this clone was digested with XhoI, two fragments were shown to hybridize to the pul-1 probe. This indicates there is an internal XhoI site in the pul-1 probe.

ii. Orientation of the Genomic Clone

The presence of a XhoI site in the clone made it possible to easily determine the orientation of the genomic DNA relative to the amino-terminal end of the clone. The pul-1 probe was isolated by PCR amplification using primers SEQ ID NO: 8 (amino terminal amino acid sequence) and SEQ ID NO: 9 (41.0 kd CNBr fragment). These primers flank the internal XhoI restriction site in the genomic clone. By using the 41-3'b PCR primer to probe the XhoI digested Southern blots (Southern, J. Mol. Biol. 98, 503 (1975)) the 8.0 kbp XhoI fragment which represents the 3'-end of the "tentative" pullulanase was identified. A 4.3 kbp BamHI fragment was isolated from this XhoI fragment to be used to probe the rice cDNA library.

4. Isolation and Characterization of a Rice Pullulanase cDNA Clone a. Screening the Rice Flowering Stage cDNA Library for Pullulanase i. cDNA Library

The rice flowering stage cDNA library was purchased from Dr. Susan Wessler, U. of Georgia, Athens. It was constructed in a Lambda gt10 phage vector and used Nato rice CI 8998 mRNA.

ii. Hybridization Probes and Primary Library Screening

The 4.3 kbp BamHI genomic clone 9-2 fragment was used to screen 180,000 recombinant phage using standard procedures (Maniatis, et al. supra 1982). Ten positive plaques were found. High titer lysates (Silhavy, et al., 1984) were prepared and the cDNA clones were screened a second time.

iii. Second cDNA Library Screen

Two duplicate filters were made of the ten positive recombinant phage clones and hybridized with different probes, i.e. pul-1 and the BamHI (4.3 kbp) genomic clone fragment (Maniatis, et al., supra. 1982). The BamHI probe will identify any pullulanase cDNA clone because it represents a large portion of the 3'-end of the pullulanase gene. If the pul-1 probe hybridizes to a cDNA clone this would be an indication that the entire or almost the entire gene was present because this probe represents the 5'-end of the gene. Of the ten cDNA clones that hybridized to the BamHI probe only one hybridized to the pul-1 probe. This clone was designated "cDNA clone 6-1".

iv. Restriction Enzyme Mapping the cDNA Clone

A restriction enzyme map was determined for the pullulanase cDNA clone 6-1 in a similar manner as for the genomic pullulanase genomic clones. The pullulanase insert was removed from the Lambda gt10 vector as two EcoRI fragments, 2.5 kbp and 0.44 kbp. Both fragments were subcloned into an appropriate vector and designated pPB/2.5pullulanase and pPB/.44pullulanase.

b. Confirmation of Pullulanase Authenticity by DNA Sequence Analysis

A partial nucleotide sequence of genomic clone 9-2 and cDNA clone 6-1 were determined, according to the dideoxy sequence method (Sanger, et al. Proc. Nat'l Acad. Sci USA 74:5463 (1977)). Based on known amino acid data, they were confirmed as authentic pullulanase clones.

5. Pullulanase DNA Sequence Analysis

Five restriction fragments of the pullulanase cDNA clone 6-1 were subcloned into the appropriate restriction sites of Bluescript SK+ sequencing vector (Stratagene, LaJolla, Calif.). The entire base sequence of cDNA clone 6-1 was determined (Sanger, et al., supra)

The DNA sequence analysis of cDNA clone 6-1 showed the first 13 amino acid residues of the mature pullulanase protein were not present in its DNA sequence. The actual DNA sequence for these amino acids was determined by DNA sequence analyses of the pullulanase PCR fragment pul-1 and genomic clone 9-2. Further, the DNA sequence analyses of the amino-terminal end of the pullulanase genomic clone 9-2 revealed no in-frame methionine codon (translational iniation codon). The primary translation product of the pullulanase mRNA may contain a signal sequence responsible for transporting the pullulanase from one part of the plant to another, a sequence responsible for maintaining the stability of the enzyme (pullulanase may be a proenzyme, such as ribonuclease), or a single methionine. Each of these protein sequences could have been removed during protein transport or maturation (processing). The pullulanase amino acid sequence information in SEQ ID NO: 7 represents the mature, processed protein.

SEQ ID NO: 1 shows the entire nucleotide sequence for the mature pullulanase enzyme. The coding region of the mature pullulanase has 2646 bp (882 amino acid residues). An additional 342 bp consists of the 3'-untranslated region which contains the rice transcriptional termination and polyadenylation signals. The calculated molecular weight of pullulanase is 98695 daltons and the pI=5.39. There are potentially nine glycosylation sites, Asn Xaa Ser/Thr. There are also nine cysteine residues, potential cross-linking sites.

C. Expression of Rice Pullulanase in Saccharomyces Cerevisiae

The following cloning strategy was developed to express the rice pullulanase gene in Saccharomyces. The pullulanase gene regulatory cassette for yeast expression consisted of the yeast MFα1 promoter and secret on signal (which contains the translational initiation codon methionine), and the rice transcriptional termination and polyedenylation signals. This pullulanase regulatory cassette with the pullulanase gene would be combined with the appropriate plasmid and introduced into a suitable host as a autonomously replicating plasmid or integrated into the chromosome. The pullulanase will be secreted into the medium where it can be isolated and assayed for pullulanase activity by methods known in the art.

The preferred expression vector was pSEY210 MFα1-SUC2 (Emr, et al., *Proc. Nat'l Acad Sci USA* 80:7080, 1983) a 2 micron based, high copy plasmid which carries both the MFα1 promoter and secretion signal but no transcriptional termination signal. The termination signal in this vector would be removed when the SUC2 gene is excised. Other expression vectors with different promoter or promoter-secretion signals would also be suitable.

It is essential to maintain a proper reading frame at the junction of the MFα1 secretion signal (HindIII site) and the pullulanase gene. The pullulanase gene could not be directly combined to the MFα1 secretion signal because there was more than one HindIII site in the pullulanase gene. As a result, specific fragments of the gene were isolated and cloned into the MFα1 expression vector in phases described below. The construction of the MFα1 pullulanase expression vector was facilitated by the presence of two unique restriction enzyme sites in the pullulanase cDNA clone, HpaI at the 5'-end and KpnI at the 3'-end. SEQ ID NO: 2 describes the pullulanase sequence that was expressed.

Polymerase chain reaction technology was chosen to isolate the 5'- and 3'-end fragments of the pullulanase gene. The DNA sequences for these regions could also be chemically synthesized and assembled into the expression vector by methods known in the art. In general, PCR was used to amplify 147 bp of the 5'-end and 701 bp of the 3'- end and these PCR fragments were subsequently cloned into the MFα1 expression vector. The 701 bp 3'-end included approximately 342 bp of the 3'-untranslated region of the pullulanase gene. This region contained the pullulanase transcriptional termination and polyadenylation signals which were similar in structure to the yeast signals and may prove to be functional in this case.

By using PCR, the DNA sequence of eleven of the thirteen amino acids that were missing from the amino terminal end of the pullulanase cDNA clone were replaced. This was done because the enzyme may be inactive without them. In order to add a HindIII site, maintain the proper reading frame, and have the least disruption of the pullulanase gene, the initial glutamine and glycine were eliminated from the DNA sequence. FIG. 1 is a diagram of the junction between the MFα1 region and the first two amino acids of the pullulanase of the present invention. SEQ ID NO: 10 through SEQ ID NO: 14 represent those sequences illustrated in FIG. 1.

The remaining 2307 bp of the pullulanase coding region was isolated from pPB/2.5pullulanase and inserted last. The pPB/pullulanase plasmid was then transformed into a suitable strain of *Saccharomyces cerevisiae* and assayed for pullulanase activity.

1. Polymerase Chain Reaction

In order to place the rice pullulanase gene under the control of the MFα1 promoter, a strategy was developed in which the gene had to be assembled sequentially in three phases. Each phase was represented by a specific DNA fragment of the pullulanase gene. PCR was used to isolated two of the gene fragments. The construction of the pPB/pullulanase vector was facilitated by the presence of two unique restriction enzyme sites in the pullulanase cDNA clone, HpaI at the 5'-end and KpnI at the 3'-end.

2. 3'pullulanase PCR amplification.

Figure 3:
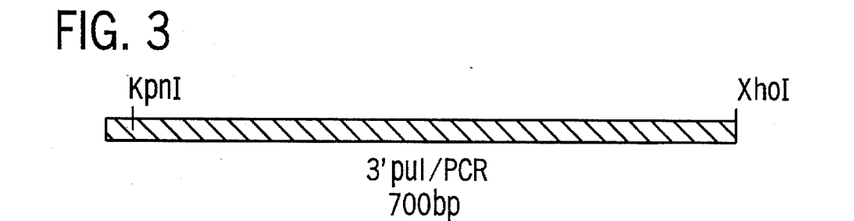
FIG. 3 is a diagram of the PCR amplification of the 3' region of the pullulanase cDNA clone.

The 3'-end of the pullulanase clone was constructed first because the PCR product was larger (See FIG. 3). The 3'-PCR primers were: primer A, 5'-GGGTTCGCTTTCA-CAACACA (SEQ ID NO: 3) and primer B, 5'-CGCTC-GAGATGAGTATTTCTTCCAGGGTA (SEQ ID NO: 4). Primer B contains a XhoI restriction site. The pullulanase cDNA clone was used as the target DNA for the PCR reaction. The 3'pul/PCR product (701 bp of the 3' -end) contained part of the 3'-coding region (includes the KpnI site) and the entire 3'-untranslated region of the cDNA clone. The entire 3'-untranslated region was included because both the transcriptional termination and polyadenylation signals of the rice gene were located in this region.

As a result the pullulanase gene expressed in yeast may terminate and be polyadenylated as it would be in the rice plant. In yeast, it has been reported the presence of a transcriptional termination signal increases the translational efficiency and stability of the mRNA (Zaret and Sherman, J. Mol. Biol. 177:107, 1979), resulting in greater protein production. The similarity of the transcriptional and polyadenylation signals of rice to yeast may also act to increase pullulanase production. Yeast transcription termination signals have been characterized (Romanos, et al., *Yeast*, 8:423 (1992)) and could be adapted for use by one skilled in the art.

3. 5'pullulanase PCR amplification

Figure 2:
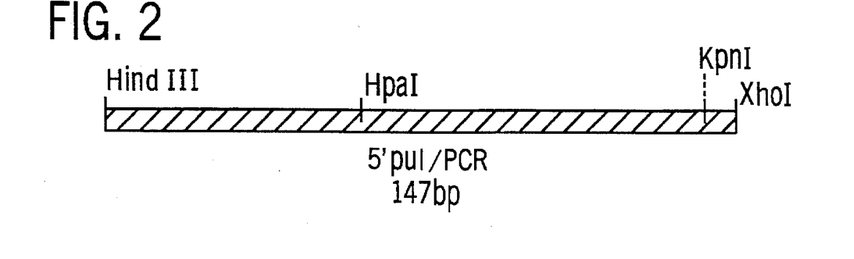
FIG. 2 is a diagram of PCR amplification of the 5' region of the pullulanase genomic clone.

PCR amplification of the 5'-end of the pullulanase (see FIG. 2) included the restoration of the DNA sequence of the missing amino acids in the cDNA clone and provided a HindIII restriction site for ligation with the MFα1 promoter/ secretion signal. The 5'-PCR primers were: primer A, 5'-AAGCTTTCGTGACGGATGCGAGGGCATA with a HindIII restriction site (SEQ ID NO: 5) and primer B, 5'-CTCGAGGGTACCATGAAAGGCCCCATCAGATA with a KpnI-XhoI restriction sites (SEQ ID NO: 6). By using the pullulanase genomic clone 9-2 as the PCR target DNA (rice genomic DNA could also be used), the 5'-PCR primers were designed to flank the DNA sequence of eleven of the thirteen missing amino acids and the unique HpaI site. In order to get proper in-frame reading of the α-factor secretion signal and the pullulanase gene, a HindIII site was necessary at the ligation junction. By eliminating the glutamine and glycine and beginning at the phenylalanine only two amino acids would be lost from the pullulanase gene and no extra amino acids would have to be added (see FIG. 1). As a result the 5'pul/PCR fragment was 147 bp long with a HindIII restriction site on the 5'-end and a KpnI-XhoI sites at the 3'-end.

4. TA-cloning PCR fragments

Both the 3'- and 5'-pullulanase PCR products (701 bp and 147 bp, respectively) were first subcloned into an Invitrogen (San Diego, Calif.) TA-cloning vector, pCR™II. This cloning system takes advantage of the activity of the thermostable polymerase used in PCR that add, in a non-template dependent manner, single dATP at the 3'-end of all duplex PCR molecules. The pCR™II vector contains a single 3'-T overhang which can directly ligate with the A-overhang of the PCR product. By taking this intermediate step, clean restriction sites were generated, which aided ligation into the MFα1 expression vector. Other methods can be envisioned, by those skilled in the art, to subclone the PCR fragments into other suitable vectors which would achieve the same results. All the fragments used for subcloning were separated by agarose gel electrophoresis, isolated by electroelution, and concentrated by column chromatography. By using these procedures the fragments were isolated free of any ligation or transformation inhibitors.

5. Subcloning 3'pul/PCR into pSEY210

Figure 4:
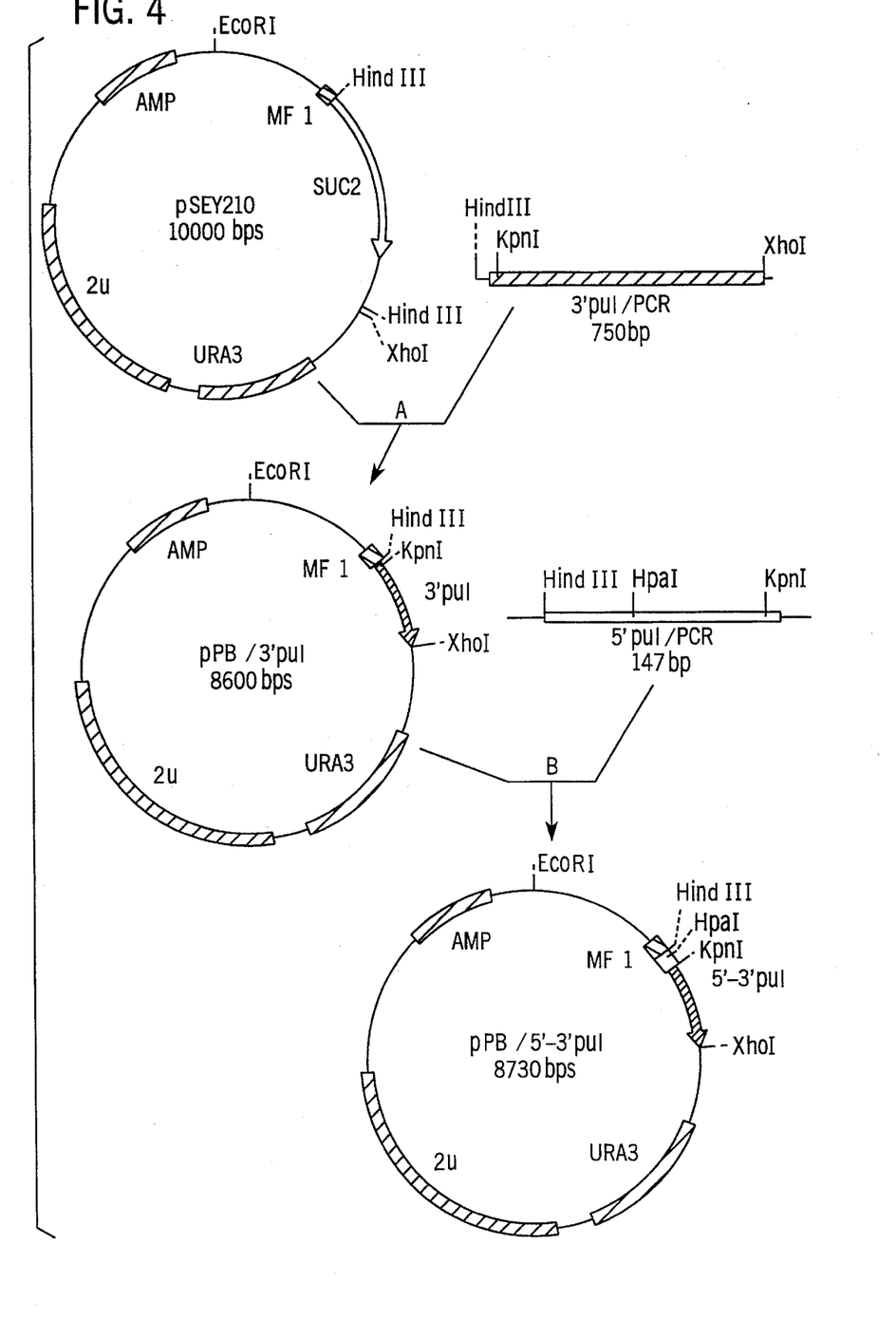
FIG. 4 is a diagram of the creation of pPB/3'pul-8.6 kb and pPB/5'-3'pul-8.73 kb.

The 3'pullulanase/PCR fragment was then excised from the pCR™II vector as a 755 bp HindIII/XhoI fragment ("A" in FIG. 4). This fragment carries approximately 54 bp of the pCR™II vector which was subsequently removed. The 3'-HindIII/XhoI fragment was cloned into the pSEY210 HindIII/XhoI site (the SUC2 gene is removed) and transformed into E. coli strain DH5α (Bethesda Research Laboratories). These subclones were designated "pPB/3'pullulanase-8.6 kb".

Figure 6:
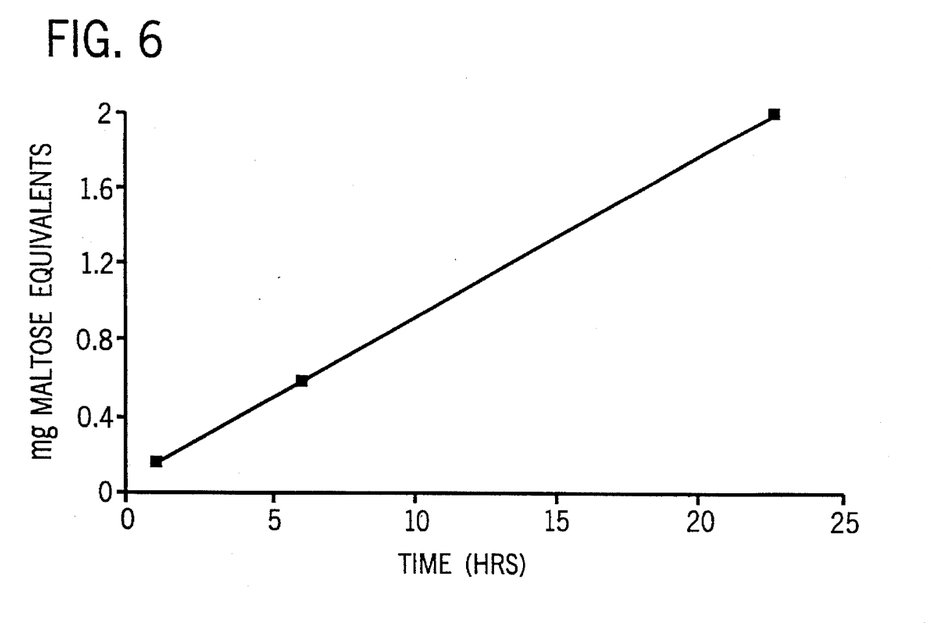
FIG. 6 is a graph of pullulanase activity for a yeast transformant of the present invention.

6. Subcloning 5'pul/PCR into pPB/3'pullulanase pPB/3'pullulanase ("B" in FIG. 6b), was digested with HindIII/KpnI, ligated with the 147 bp HindIII/KpnI 5'pullulanase/PCR fragment excised from pCR™II, and transformed into E. coli DH5α cells. These clones were designated pPB/5'-3'pullulanase-8.73 kb.

Figure 5:
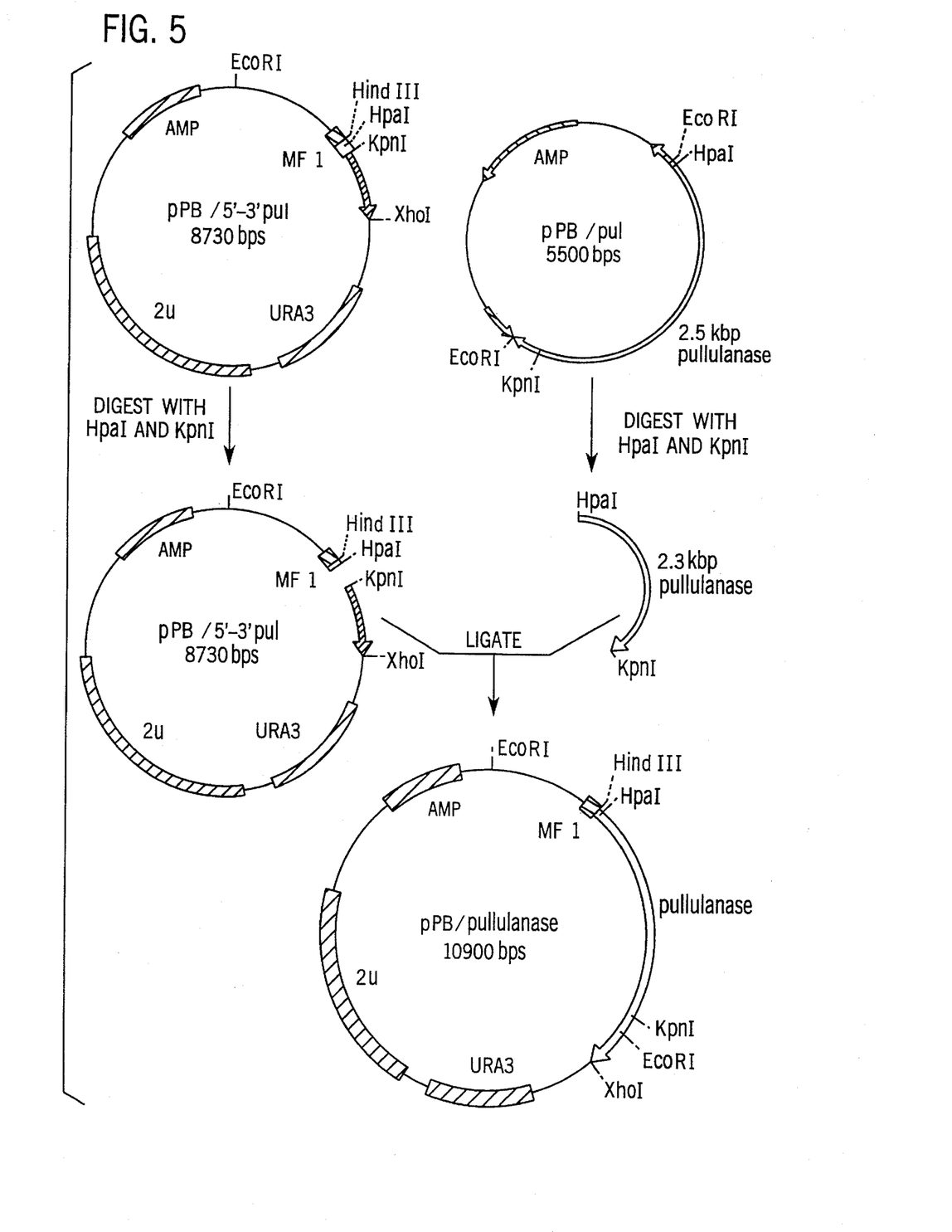
FIG. 5 is a diagram of the creation of pPB/pullulanase-10.9 kb.

7. Subcloning the 2.3 kbp Fragment of DPB/2.5 Pullulanase Clone into pPB/5'-3'pullulanase pPB/2.5 pullulanase and pPB/5'-3'pullulanase were digested with HpaI/KpnI. The 2.3 kbp pullulanase fragment of pPB/2.5 pullulanase was isolated and ligated into pPB/5' -3'pullulanase and transformed into E. coli DH5α. These clones were designated pPB/pullulanase (10.9 kb). FIG. 5 describes this procedure.

8. Transformation of pPB/pullulanase into Yeast

Yeast strain SEY2102 (MATα; ura3–52; leu2-3,–112; his4– 519 (Emr, et al., Proc. Nat'l Acad. Sci USA, 80:7080, 1983)) was transformed with pPB/pullulanase using a procedure in which the plasmid was incubated overnight in the presence of the host yeast and a PEG/lithium acetate mixture (Elble, Biotechniques 13:18 1992). The transformant cells were plated on to selective media the following day. After five days approximately 150 transformants were found.

The transformed *Saccharomyces cerevisiae* yeast strain SEY2102 containing the pPB/pullulanase construct was deposited under the terms of the Budapest Treaty on Apr. 14, 1994 with the American Type Culture Collection, 12301 Parklawn Drive, Rockville, Md. 20852 under ATCC Accession No. 74281.

9. Analysis of pPB/pullulanase Yeast Transformants for Pullulanase Activity

A pPB/pullulanase yeast transformant was assayed for pullulanase activity in enriched medium (YPD—1% yeast, 2% peptone, 2% dextrose). The transformant and SEY2102 control were each grown in 200 ml of YPD media for approximately 36– 40 hours; glucose was no longer present in the medium. The yeast cells were removed by centrifugation and the broth was concentrated by ammonium sulfate precipitation (60%). After five hours mixing at 4° C. the precipitate was resuspended in 10 ml of 0.2N sodium acetate, pH 5.0 and dialyzed overnight against 0.2N NaOAC; pH 5.0. (The samples were further concentrated with polyethylene glycol.) Two ml of the concentrated broths of pPB/pullulanase and SEY2102 were placed in an equal volume of 0.2N NaOAC/1% pullulan and assayed for the presence of pullulanase reducing activity at 50° C. The reaction was stopped by the addition of an equal volume of 3, 5-dinitrosalicylic acid. The sample was boiled for ten minutes, diluted with ten ml of water, and read at $A_{540nm}$. The transformant broth showed pullulanase activity relative to the SEY2102 control. The results in FIG. 6 show a linear increase in pullulanase activity over time as measured by milligram maltose equivalents. Milligram maltose equivalents were measured from a maltose calibration curve by methods known in the art. Bernfield, P., *Advances in Enzymology XII* (1951).

---

I claim:

1. A DNA construct capable of expressing an active rice pullulanase enzyme comprising a coding sequence according to that of SEQ ID NO:1 wherein the termination codon occurs at nucleotide positions 2647–2649, and regulatory sequences allowing expression of the coding sequence in a microorganism host selected from the group consisting of *Saccharomyces, Bacillus, Aspergillus, Pichia, Kluyveromyces*, and *Escherichia coli*, wherein said regulatory sequences are not operatively linked in nature with the coding sequence.

2. The DNA construct of claim 1 wherein the regulatory sequences include the MFα1 promoter.

3. The DNA construct of claim 2 wherein the construct is contained within the pSEY210 vector.

4. The DNA construct of claim 1 wherein the microorganism host is *Saccharomyces cerevisiae*.

5. A rice pullulanase expressed by the DNA construct of claim 1.

6. A microorganism transformed with the DNA construct of claim 1, which organism is selected from the group consisting of *Saccharomyces, Bacillus, Aspergillus, Pichia, Kluyveromyces*, and *Escherichia coli*.

7. The microorganism of claim 6 wherein the microorganism is *Saccharomyces cerevisiae*.

8. A DNA construct capable of expressing an active rice pullulanase enzyme comprising a coding sequence according to that of SEQ ID NO:2 wherein the termination codon occurs at nucleotide positions 2641–2643, and regulatory sequences allowing expression of the coding sequence in a microorganism host selected from the group consisting of *Saccharomyces, Bacillus, Aspergillus, Pichia, Kluyveromyces*, and *Escherichia coli*, wherein said regulatory sequences are not operatively linked in nature with the coding sequence.

9. The DNA construct of claim 8 wherein the regulatory sequences include the MFα1 promoter.

10. The DNA construct of claim 9 wherein the construct is contained within the pSEY210 vector.

11. The DNA construct of claim 8 wherein the microorganism host is *Saccharomyces cerevisiae*.

12. A rice pullulanase expressed by the DNA construct of claim 8.

13. A microorganism transformed with the DNA construct of claim 8, which organism is selected from the group consisting of *Saccharomyces, Bacillus, Aspergillus, Pichia, Kluyveromyces,* and *Escherichia coli.*

14. The microorganism of claim 13 wherein the microorganism is *Saccharomyces cerevisiae.*

15. A yeast according to ATCC Designation No. 74281.

16. A DNA construct capable of expressing an active rice pullulanase enzyme comprising a coding sequence according to that of SEQ ID NO:7 wherein the codon specifying the carboxyl-terminal amino acid of the pullulanase occurs at nucleotide positions 2644–2646, and regulatory sequences allowing expression of the coding sequence in a microorganism host selected from the group consisting of *Saccharomyces, Bacillus, Aspergillus, Pichia, Kluyveromyces,* and *Escherichia coli,* wherein said regulatory sequences are not operatively linked in nature with the coding sequence.

17. The DNA construct of claim 16 wherein the regulatory sequences include the MFα1 promoter.

18. The DNA construct of claim 17 wherein the construct is contained within the pSEY210 vector.

19. The DNA construct of claim 16 wherein the microorganism host is *Saccharomyces cerevisiae.*

20. A rice pullulanase expressed by the DNA construct of claim 16.

21. A microorganism transformed with the DNA construct of claim 16, which organism is selected from the group consisting of *Saccharomyces, Bacillus, Aspergillus, Pichia, Kluyveromyces,* and *Escherichia coli.*

22. The microorganism of claim 21 wherein the microorganism is *Saccharomyces cerevisiae.*

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 2988 base pairs
( B ) TYPE: nucleic acid ( C ) STRANDEDNESS: double
( D ) TOPOLOGY: linear ( i i ) MOLECULE TYPE: cDNA ( x i ) SEQUENCE DESCRIPTION: SEQ ID NO:1:

| | | | | | | |
|---|---|---|---|---|---|---|
| CAGGGGTTCG | TGACGGATGC | GAGGGCATAC | TGGGTGACAA | GGTCTCTGAT | TGCCTGGAAT | 60 |
| GTTAACGATC | AAGACACCTC | CCTCTTCCTG | TATGCAAGCA | GAGATGCCAC | GATGCACGTA | 120 |
| TCTGATGGGG | CCATTCATGG | TTATGATTCA | AAAATTGAAC | TCGAGCCAGA | ACATGCCAGC | 180 |
| CTTCCAGACA | ATGTGGCTGA | GAAGTTCCCG | TTTATCAGAA | GTTACAGAAC | CTTCAGAGTC | 240 |
| CCTAGCTCTG | TTGATGTCGC | GAGCCTTGTG | AAATGCCAAC | TGGCTGTCGC | TTCTTATGAT | 300 |
| GCTCATGGGA | GGCGTCAAGA | TGTTACTGGA | TTGCAACTAC | CTGGTGTATT | GGATGACATG | 360 |
| TTTGCTTATA | CTGGACCACT | TGGTGCAGTT | TTCAGTGATA | AAGATGTGGA | CCTCTACCTT | 420 |
| TGGGCTCCTA | CAGATCAGGA | TGTTAGAGTA | TGCTTCTATG | ATGGTCCAGC | AGGACCTTTA | 480 |
| CTGCAAACTG | TGCAACTCAA | GGAGTTAAAT | GGTGTGTGGA | GTGTTACTGT | ACCAAGATAC | 540 |
| CGGGAGAACC | AGTACTATTT | GTATGAAGTT | AAGGTTTATC | ATCCTAGTAC | ATCACAAGTT | 600 |
| GAGAAATGTT | TAGCTGATGA | TCCCTATGCC | AGAGGGCTTT | CTGCCAATGG | CACGCGGACT | 660 |
| TGGTTGGGTG | ACATTAATAG | TGAAACTTTA | AGCCAGCTT | CCTGGGATGA | ATTGTCAGAT | 720 |
| GAGAAGCCAA | ACCTTGAGTC | CTTCTCTGAC | ATAAGCATCT | ATGAGTTGCA | TATTCGTGAT | 780 |
| TTCAGTGCTC | ATGATAGCAC | AGTGGACTGT | AACTCTCGTG | GAGGATTTCG | TGCATTTACA | 840 |
| TTTCAGGATT | CAGCAGGAAT | ACGTCACCTG | AGAAAATTGT | CTGCTGCTGG | CTTGACTCAT | 900 |
| GTTCATTTGT | TACCAAGCTT | TCATTTTGCT | AGTGTTGATG | ACAACACAAG | CAATTGGAAA | 960 |
| CTTGTTGATG | AGGCTCAGCT | GGCAAAACTC | CCTCCAGGTT | CAGATGAGCA | ACAAGCTGCA | 1020 |
| ATAGTATCTA | TTCAGCAAGA | GGATCCTTAC | AATTGGGGGT | ATGACCCTGT | ACTCTGGGGG | 1080 |
| GTTCCAAAAG | GAAGCTATGC | AAGTAACCCA | GATGGTCCTA | GTCGTATTAT | TGAATACCGA | 1140 |
| CAGATGGTTC | AGGCCCTGAA | TCGCATAGGT | CTTCGTGTTG | TCATGGATGT | TGTATACAAT | 1200 |
| CATTTAGACT | CAAGTGGCCC | CTTTGGTGTC | TCCTCAGTGC | TTGACAAGAT | TGTTCCTGGA | 1260 |
| TATTACCTTA | GGCGGAACGT | TAATGGTCAG | ATCGAAAACA | GTGCGGCTAT | GAACAATACA | 1320 |
| GCAAGTGAGC | ATTTCATGGT | TGATAGGTTA | ATCGTGGATG | ACCTTTTAAA | TTGGGCAATA | 1380 |
| AATTACAAAG | TTGATGGGTT | CAGATTTGAT | CTTATGGGGC | ATATCATGAA | AAATACCATG | 1440 |
| ATAAGAGCAA | AATCTGCTAT | TCGAAGCCTT | ACGAGGGATG | TACATGGAGT | GGATGGTTCA | 1500 |
| AAGATATACT | TGTATGGTGA | AGGATGGGAC | TTTGGTGAGG | TTGCACAAAA | TAAGCGTGGA | 1560 |
| ATAAATGCAT | CCCAGATTAA | TATGAGTGGC | ACAGGAATTG | GTAGTTTCAA | CGATAGGATC | 1620 |
| CGCGATTCTG | TTAATGGGGG | TAATCCATTT | GGTAATCCTC | TACAGCAAGG | CTTTTCTACC | 1680 |
| GGTCTGTTCT | TGGAGCCGAA | TGGATATTAT | CAGGGTAATG | AAGCAGATAC | CAGGCGTGAA | 1740 |
| CTTGCTACAT | ATGCTGATCA | CATACAGATC | GGGCTAGCTG | GTAACCTGAA | GGATTATGTA | 1800 |
| CTAAGAACTC | ATACTGGAGA | AGCTAAGAAG | GGATCAGACA | TTTACACTTG | GATGGATCA | 1860 |
| CCAGTTGGCT | ATACTTCATC | CCCTGTAGAA | ACTATAAACT | ATGTTTCTGC | TCATGATAAT | 1920 |
| GAGACTGTGT | GTGATATTGT | CAGTATAAAG | ACCCCAATTG | GCCTCTCGAT | TGATGAGAAA | 1980 |
| TGCAGGATAA | ATCATGTGGC | TTCAAGCATG | ATCGCGTTAT | CCCAGGGAAT | ACCTTTCTTC | 2040 |
| CATGCTGGTG | ATGAGATACT | GAGATCTAAG | TCACTTGATC | GAGATTCATA | TAATTCTGGT | 2100 |
| GATTGGTTTA | ACAAGCTTGA | TTTTACATAT | GAAACGAACA | ATTGGGGCGT | AGGACTTCCT | 2160 |
| CCAAGAGATA | AGAATGAAGA | AAATTGGCAT | TTGATAAAAC | CAAGATTGGA | AAACCCATCT | 2220 |

| | | | | | |
|---|---|---|---|---|---|
|TTCAGACCTT|CAAAAAATCA|CATTCTTTCT|GTCTTCGATA|ATTTTGTTGA|CATCTTGAAG|2280
|ATCAGATACT|CCTCACCGCT|CTTTCGTTTG|AGTACAGCAA|GTGACATTGA|GCAAAGGGTT|2340
|CGCTTTCACA|ACACAGGTCC|CTCGATGGTA|CCAGGAGTTA|TTGTCATGAG|CATTAAAGAT|2400
|GCTCAAAATG|AAAAATGTGA|AATGGCCCAG|TTAGATAAAA|ACTTCTCTTA|TGTCGTGACG|2460
|ATCTTCAATG|TCTGTCCACA|TGAAGTGTCT|ATAGAAATCC|ATGATCTTGC|TTCGTTGGGG|2520
|CTTGAATTAC|ATCCTATTCA|GGTGAATTCA|TCGGATGCTC|TAGTCAGGCA|GTCAGCATAC|2580
|GAGGCGTCCA|AAGGTCGATT|CACCGTGCCA|AGAAGAACAA|CTGCAGTGTT|TGTTCAACCT|2640
|AGATGTTGAT|GCCCTTGGGA|AAACGTTCAT|ATTATGTCGA|AAAATATGAA|TGAAGAATAA|2700
|GAGAAGAAAA|ATCCTCAAGT|TGAATATTTC|TGAAGAAATA|AATGGAAGAA|TATGGAGAGA|2760
|CTGGCTAGTA|TACTAATAGA|GTAATAGTAT|AGTTTTAGAG|AAAAAAAAAA|GCATACTTGT|2820
|AGTATCGCAT|AAAGTGCCCA|GGTTTCGGCA|TGCTTTGGCA|TCTTTGTAAG|GGTATTGTAT|2880
|TGTACTGTTG|TCATTATCAC|ACACACNCAC|AAAAAAAGAC|ATACTTATGT|TTACATGGAA|2940
|ATATGGCATG|CTAAGTAAAT|AAAAATGCTC|CCTTTGTTTC|ACAAAAAA| |2988

(2) INFORMATION FOR SEQ ID NO:2:

(i) SEQUENCE CHARACTERISTICS:
        (A) LENGTH: 2982 base pairs
        (B) TYPE: nucleic acid
        (C) STRANDEDNESS: double
        (D) TOPOLOGY: linear     (ii) MOLECULE TYPE: Oligonucleotide     (xi) SEQUENCE DESCRIPTION: SEQ ID NO:2:

| | | | | | |
|---|---|---|---|---|---|
|TTCGTGACGG|ATGCGAGGGC|ATACTGGGTG|ACAAGGTCTC|TGATTGCCTG|GAATGTTAAC|60
|GATCAAGACA|CCTCCCTCTT|CCTGTATGCA|AGCAGAGATG|CCACGATGCA|CGTATCTGAT|120
|GGGGCCATTC|ATGGTTATGA|TTCAAAAATT|GAACTCGAGC|CAGAACATGC|CAGCCTTCCA|180
|GACAATGTGG|CTGAGAAGTT|CCCGTTTATC|AGAAGTTACA|GAACCTTCAG|AGTCCCTAGC|240
|TCTGTTGATG|TCGCGAGCCT|TGTGAAATGC|CAACTGGCTG|TCGCTTCTTA|TGATGCTCAT|300
|GGGAGGCGTC|AAGATGTTAC|TGGATTGCAA|CTACCTGGTG|TATTGGATGA|CATGTTTGCT|360
|TATACTGGAC|CACTTGGTGC|AGTTTTCAGT|GATAAAGATG|TGGACCTCTA|CCTTTGGGCT|420
|CCTACAGATC|AGGATGTTAG|AGTATGCTTC|TATGATGGTC|CAGCAGGACC|TTTACTGCAA|480
|ACTGTGCAAC|TCAAGGAGTT|AAATGGTGTG|TGGAGTGTTA|CTGTACCAAG|ATACCGGGAG|540
|AACCAGTACT|ATTTGTATGA|AGTTAAGGTT|TATCATCCTA|GTACATCACA|AGTTGAGAAA|600
|TGTTTAGCTG|ATGATCCCTA|TGCCAGAGGG|CTTTCTGCCA|ATGGCACGCG|GACTTGGTTG|660
|GGTGACATTA|ATAGTGAAAC|TTTAAAGCCA|GCTTCCTGGG|ATGAATTGTC|AGATGAGAAG|720
|CCAAACCTTG|AGTCCTTCTC|TGACATAAGC|ATCTATGAGT|TGCATATTCG|TGATTTCAGT|780
|GCTCATGATA|GCACAGTGGA|CTGTAACTCT|CGTGGAGGAT|TCGTGCATT|TACATTTCAG|840
|GATTCAGCAG|GAATACGTCA|CCTGAGAAAA|TTGTCTGCTG|CTGGCTTGAC|TCATGTTCAT|900
|TTGTTACCAA|GCTTTCATTT|TGCTAGTGTT|GATGACAACA|CAAGCAATTG|GAAACTTGTT|960
|GATGAGGCTC|AGCTGGCAAA|ACTCCCTCCA|GGTTCAGATG|AGCAACAAGC|TGCAATAGTA|1020
|TCTATTCAGC|AAGAGGATCC|TTACAATTGG|GGGTATGACC|CTGTACTCTG|GGGGGTTCCA|1080
|AAAGGAAGCT|ATGCAAGTAA|CCCAGATGGT|CCTAGTCGTA|TTATTGAATA|CCGACAGATG|1140
|GTTCAGGCCC|TGAATCGCAT|AGGTCTTCGT|GTTGTCATGG|ATGTTGTATA|CAATCATTTA|1200

| | | | | | | |
|---|---|---|---|---|---|---|
| GACTCAAGTG | GCCCCTTTGG | TGTCTCCTCA | GTGCTTGACA | AGATTGTTCC | TGGATATTAC | 1260 |
| CTTAGGCGGA | ACGTTAATGG | TCAGATCGAA | AACAGTGCGG | CTATGAACAA | TACAGCAAGT | 1320 |
| GAGCATTTCA | TGGTTGATAG | GTTAATCGTG | GATGACCTTT | TAAATTGGGC | AATAAATTAC | 1380 |
| AAAGTTGATG | GGTTCAGATT | TGATCTTATG | GGGCATATCA | TGAAAAATAC | CATGATAAGA | 1440 |
| GCAAAATCTG | CTATTCGAAG | CCTTACGAGG | GATGTACATG | GAGTGGATGG | TTCAAAGATA | 1500 |
| TACTTGTATG | GTGAAGGATG | GGACTTTGGT | GAGGTTGCAC | AAAATAAGCG | TGGAATAAAT | 1560 |
| GCATCCCAGA | TTAATATGAG | TGGCACAGGA | ATTGGTAGTT | TCAACGATAG | GATCCGCGAT | 1620 |
| TCTGTTAATG | GGGGTAATCC | ATTTGGTAAT | CCTCTACAGC | AAGGCTTTTC | TACCGGTCTG | 1680 |
| TTCTTGGAGC | CGAATGGATA | TTATCAGGGT | AATGAAGCAG | ATACCAGGCG | TGAACTTGCT | 1740 |
| ACATATGCTG | ATCACATACA | GATCGGGCTA | GCTGGTAACC | TGAAGGATTA | TGTACTAAGA | 1800 |
| ACTCATACTG | GAGAAGCTAA | GAAGGGATCA | GACATTTACA | CTTGGGATGG | ATCACCAGTT | 1860 |
| GGCTATACTT | CATCCCCTGT | AGAAACTATA | AACTATGTTT | CTGCTCATGA | TAATGAGACT | 1920 |
| GTGTGTGATA | TTGTCAGTAT | AAAGACCCCA | ATTGGCCTCT | CGATTGATGA | GAAATGCAGG | 1980 |
| ATAAATCATG | TGGCTTCAAG | CATGATCGCG | TTATCCCAGG | GAATACCTTT | CTTCCATGCT | 2040 |
| GGTGATGAGA | TACTGAGATC | TAAGTCACTT | GATCGAGATT | CATATAATTC | TGGTGATTGG | 2100 |
| TTTAACAAGC | TTGATTTTAC | ATATGAAACG | AACAATTGGG | GCGTAGGACT | TCCTCCAAGA | 2160 |
| GATAAGAATG | AAGAAAATTG | GCATTTGATA | AAACCAAGAT | TGGAAAACCC | ATCTTTCAGA | 2220 |
| CCTTCAAAAA | ATCACATTCT | TTCTGTCTTC | GATAATTTTG | TTGACATCTT | GAAGATCAGA | 2280 |
| TACTCCTCAC | CGCTCTTTCG | TTTGAGTACA | GCAAGTGACA | TTGAGCAAAG | GGTTCGCTTT | 2340 |
| CACAACACAG | GTCCCTCGAT | GGTACCAGGA | GTTATTGTCA | TGAGCATTAA | AGATGCTCAA | 2400 |
| AATGAAAAAT | GTGAAATGGC | CCAGTAGAT | AAAACTTCT | CTTATGTCGT | GACGATCTTC | 2460 |
| AATGTCTGTC | CACATGAAGT | GTCTATAGAA | ATCCATGATC | TTGCTTCGTT | GGGGCTTGAA | 2520 |
| TTACATCCTA | TTCAGGTGAA | TTCATCGGAT | GCTCTAGTCA | GGCAGTCAGC | ATACGAGGCG | 2580 |
| TCCAAAGGTC | GATTCACCGT | GCCAAGAAGA | ACAACTGCAG | TGTTTGTTCA | ACCTAGATGT | 2640 |
| TGATGCCCTT | GGGAAAACGT | TCATATTATG | TCGAAAAATA | TGAATGAAGA | ATAAGAGAAG | 2700 |
| AAAAATCCTC | AAGTTGAATA | TTTCTGAAGA | AATAAATGGA | AGAATATGGA | GAGACTGGCT | 2760 |
| AGTATACTAA | TAGAGTAATA | GTATAGTTTT | AGAGAAAAAA | AAAGCATAC | TTGTAGTATC | 2820 |
| GCATAAAGTG | CCCAGGTTTC | GGCATGCTTT | GGCATCTTTG | TAAGGGTATT | GTATTGTACT | 2880 |
| GTTGTCATTA | TCACACACAC | NCACAAAAAA | AGACATACTT | ATGTTTACAT | GGAAATATGG | 2940 |
| CATGCTAAGT | AAATAAAAAT | GCTCCCTTTG | TTTCACAAAA | AA | | 2982 |

( 2 ) INFORMATION FOR SEQ ID NO:3:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: Oligonucleotide     ( x i ) SEQUENCE DESCRIPTION: SEQ ID NO:3:

GGGTTCGCTT TCACAACACA                                                                   20

( 2 ) INFORMATION FOR SEQ ID NO:4:

( i ) SEQUENCE CHARACTERISTICS:
        ( A ) LENGTH: 29 bases (B) TYPE: nucleic acid
(C) STRANDEDNESS: single
(D) TOPOLOGY: linear (ii) MOLECULE TYPE: Oligonucleotide (xi) SEQUENCE DESCRIPTION: SEQ ID NO:4:

CGCTCGAGAT GAGTATTTCT TCCAGGGTA  29

(2) INFORMATION FOR SEQ ID NO:5:

(i) SEQUENCE CHARACTERISTICS:
(A) LENGTH: 28 bases
(B) TYPE: nucleic acid
(C) STRANDEDNESS: single
(D) TOPOLOGY: linear (ii) MOLECULE TYPE: Oligonucleotide (xi) SEQUENCE DESCRIPTION: SEQ ID NO:5:

AAGCTTTCGT GACGGATGCG AGGGCATA  28

(2) INFORMATION FOR SEQ ID NO:6:

(i) SEQUENCE CHARACTERISTICS:
(A) LENGTH: 32 bases
(B) TYPE: nucleic acid
(C) STRANDEDNESS: single
(D) TOPOLOGY: linear (ii) MOLECULE TYPE: Oligonucleotide (xi) SEQUENCE DESCRIPTION: SEQ ID NO:6:

CTCGAGGGTA CCATGAAAGG CCCCATCAGA TA  32

(2) INFORMATION FOR SEQ ID NO:7:

(i) SEQUENCE CHARACTERISTICS:
(A) LENGTH: 2646 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:7:

| | | | | | | |
|---|---|---|---|---|---|---|
| CAGGGGTTCG | TGACGGATGC | GAGGGCATAC | TGGGTGACAA | GGTCTCTGAT | TGCCTGGAAT | 60 |
| GTTAACGATC | AAGACACCTC | CCTCTTCCTG | TATGCAAGCA | GAGATGCCAC | GATGCACGTA | 120 |
| TCTGATGGGG | CCATTCATGG | TTATGATTCA | AAAATTGAAC | TCGAGCCAGA | ACATGCCAGC | 180 |
| CTTCCAGACA | ATGTGGCTGA | GAAGTTCCCG | TTTATCAGAA | GTTACAGAAC | CTTCAGAGTC | 240 |
| CCTAGCTCTG | TTGATGTCGC | GAGCCTTGTG | AAATGCCAAC | TGGCTGTCGC | TTCTTATGAT | 300 |
| GCTCATGGGA | GGCGTCAAGA | TGTTACTGGA | TTGCAACTAC | CTGGTGTATT | GGATGACATG | 360 |
| TTTGCTTATA | CTGGACCACT | TGGTGCAGTT | TTCAGTGATA | AAGATGTGGA | CCTCTACCTT | 420 |
| TGGGCTCCTA | CAGATCAGGA | TGTTAGAGTA | TGCTTCTATG | ATGGTCCAGC | AGGACCTTTA | 480 |
| CTGCAAACTG | TGCAACTCAA | GGAGTTAAAT | GGTGTGTGGA | GTGTTACTGT | ACCAAGATAC | 540 |
| CGGGAGAACC | AGTACTATTT | GTATGAAGTT | AAGGTTTATC | ATCCTAGTAC | ATCACAAGTT | 600 |
| GAGAAATGTT | TAGCTGATGA | TCCCTATGCC | AGAGGGCTTT | CTGCCAATGG | CACGCGGACT | 660 |
| TGGTTGGGTG | ACATTAATAG | TGAAACTTTA | AAGCCAGCTT | CCTGGGATGA | ATTGTCAGAT | 720 |
| GAGAAGCCAA | ACCTTGAGTC | CTTCTCTGAC | ATAAGCATCT | ATGAGTTGCA | TATTCGTGAT | 780 |
| TTCAGTGCTC | ATGATAGCAC | AGTGGACTGT | AACTCTCGTG | GAGGATTTCG | TGCATTTACA | 840 |

| | | | | | |
|---|---|---|---|---|---|
| TTTCAGGATT | CAGCAGGAAT | ACGTCACCTG | AGAAAATTGT | CTGCTGCTGG | CTTGACTCAT | 900
| GTTCATTTGT | TACCAAGCTT | TCATTTTGCT | AGTGTTGATG | ACAACACAAG | CAATTGGAAA | 960
| CTTGTTGATG | AGGCTCAGCT | GGCAAAACTC | CCTCCAGGTT | CAGATGAGCA | ACAAGCTGCA | 1020
| ATAGTATCTA | TTCAGCAAGA | GGATCCTTAC | AATTGGGGGT | ATGACCCTGT | ACTCTGGGGG | 1080
| GTTCCAAAAG | GAAGCTATGC | AAGTAACCCA | GATGGTCCTA | GTCGTATTAT | TGAATACCGA | 1140
| CAGATGGTTC | AGGCCCTGAA | TCGCATAGGT | CTTCGTGTTG | TCATGGATGT | TGTATACAAT | 1200
| CATTTAGACT | CAAGTGGCCC | CTTTGGTGTC | TCCTCAGTGC | TTGACAAGAT | TGTTCCTGGA | 1260
| TATTACCTTA | GGCGGAACGT | TAATGGTCAG | ATCGAAAACA | GTGCGGCTAT | GAACAATACA | 1320
| GCAAGTGAGC | ATTTCATGGT | TGATAGGTTA | ATCGTGGATG | ACCTTTAAA | TTGGGCAATA | 1380
| AATTACAAAG | TTGATGGGTT | CAGATTTGAT | CTTATGGGGC | ATATCATGAA | AAATACCATG | 1440
| ATAAGAGCAA | AATCTGCTAT | TCGAAGCCTT | ACGAGGGATG | TACATGGAGT | GGATGGTTCA | 1500
| AAGATATACT | TGTATGGTGA | AGGATGGGAC | TTTGGTGAGG | TTGCACAAAA | TAAGCGTGGA | 1560
| ATAAATGCAT | CCCAGATTAA | TATGAGTGGC | ACAGGAATTG | GTAGTTTCAA | CGATAGGATC | 1620
| CGCGATTCTG | TTAATGGGGG | TAATCCATTT | GGTAATCCTC | TACAGCAAGG | CTTTTCTACC | 1680
| GGTCTGTTCT | TGGAGCCGAA | TGGATATTAT | CAGGGTAATG | AAGCAGATAC | CAGGCGTGAA | 1740
| CTTGCTACAT | ATGCTGATCA | CATACAGATC | GGGCTAGCTG | GTAACCTGAA | GGATTATGTA | 1800
| CTAAGAACTC | ATACTGGAGA | AGCTAAGAAG | GGATCAGACA | TTTACACTTG | GGATGGATCA | 1860
| CCAGTTGGCT | ATACTTCATC | CCCTGTAGAA | ACTATAAACT | ATGTTTCTGC | TCATGATAAT | 1920
| GAGACTGTGT | GTGATATTGT | CAGTATAAAG | ACCCCAATTG | GCCTCTCGAT | TGATGAGAAA | 1980
| TGCAGGATAA | ATCATGTGGC | TTCAAGCATG | ATCGCGTTAT | CCCAGGGAAT | ACCTTTCTTC | 2040
| CATGCTGGTG | ATGAGATACT | GAGATCTAAG | TCACTTGATC | GAGATTCATA | TAATTCTGGT | 2100
| GATTGGTTTA | ACAAGCTTGA | TTTTACATAT | GAAACGAACA | ATTGGGGCGT | AGGACTTCCT | 2160
| CCAAGAGATA | AGAATGAAGA | AAATTGGCAT | TTGATAAAAC | CAAGATTGGA | AAACCCATCT | 2220
| TTCAGACCTT | CAAAAAATCA | CATTCTTTCT | GTCTTCGATA | ATTTGTTGA | CATCTTGAAG | 2280
| ATCAGATACT | CCTCACCGCT | CTTTCGTTTG | AGTACAGCAA | GTGACATTGA | GCAAAGGGTT | 2340
| CGCTTTCACA | ACACAGGTCC | CTCGATGGTA | CCAGGAGTTA | TTGTCATGAG | CATTAAAGAT | 2400
| GCTCAAAATG | AAAAATGTGA | AATGGCCCAG | TTAGATAAAA | ACTTCTCTTA | TGTCGTGACG | 2460
| ATCTTCAATG | TCTGTCCACA | TGAAGTGTCT | ATAGAAATCC | ATGATCTTGC | TTCGTTGGGG | 2520
| CTTGAATTAC | ATCCTATTCA | GGTGAATTCA | TCGGATGCTC | TAGTCAGGCA | GTCAGCATAC | 2580
| GAGGCGTCCA | AAGGTCGATT | CACCGTGCCA | AGAAGAACAA | CTGCAGTGTT | TGTTCAACCT | 2640
| AGATGT | | | | | | 2646

( 2 ) INFORMATION FOR SEQ ID NO:8:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: oligonucleotide     ( i x ) FEATURE:
        ( A ) NAME/KEY: modified_base
        ( B ) LOCATION: 6..15
        ( D ) OTHER INFORMATION: /mod_base=OTHER
            / label=Modification
            / note="N designates the base inosine."

( x i ) SEQUENCE DESCRIPTION: SEQ ID NO:8:

CARGGNTTYG TNACNGAYGC                                                                                              20

( 2 ) INFORMATION FOR SEQ ID NO:9:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear     ( i i ) MOLECULE TYPE: oligonucleotide     ( i x ) FEATURE:
        ( A ) NAME/KEY: modified_base
        ( B ) LOCATION: 18
        ( D ) OTHER INFORMATION: /mod_base=OTHER
            / label=Modification
            / note="N designates the base inosine."

( x i ) SEQUENCE DESCRIPTION: SEQ ID NO:9:

TACAARCGNA TRTGMCCNGG                                                                                              20

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: CDS
        ( B ) LOCATION: 1..15

( x i ) SEQUENCE DESCRIPTION: SEQ ID NO:10:

```
GAG  GCT  GAA  GCT  TTC                                                                                            15
Glu  Ala  Glu  Ala  Phe
  1                  5
```

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: CDS
        ( B ) LOCATION: 1..12

( x i ) SEQUENCE DESCRIPTION: SEQ ID NO:11:

```
CAG  GGG  TTC  GTG                                                                                                 12
Gln  Gly  Phe  Val
  1
```

( 2 ) INFORMATION FOR SEQ ID NO:12:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear     ( i i ) MOLECULE TYPE: cDNA ( i x ) FEATURE:
    ( A ) NAME/KEY: CDS
    ( B ) LOCATION: 1..12

( x i ) SEQUENCE DESCRIPTION: SEQ ID NO:12:

```
CTC  CGA  CTT  CGA                                                              12
Glu  Ala  Glu  Ala
 1
```

( 2 ) INFORMATION FOR SEQ ID NO:13:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: linear     ( i i ) MOLECULE TYPE: cDNA     ( i x ) FEATURE:
        ( A ) NAME/KEY: CDS
        ( B ) LOCATION: 1..6

( x i ) SEQUENCE DESCRIPTION: SEQ ID NO:13:

```
AAG  CAC                                                                         6
Phe  Val
 1
```

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear     ( i i ) MOLECULE TYPE: cDNA     ( i x ) FEATURE:
        ( A ) NAME/KEY: CDS
        ( B ) LOCATION: 1..18

( x i ) SEQUENCE DESCRIPTION: SEQ ID NO:14:

```
CTC  CGA  CTT  CGA  AAG  CAC                                                    18
Glu  Ala  Glu  Ala  Phe  Val
 1                    5
```